United States Patent [19]

Roser

[11] Patent Number: 4,891,319

[45] Date of Patent: Jan. 2, 1990

[54] PROTECTION OF PROTEINS AND THE LIKE

[75] Inventor: Bruce J. Roser, Balsham, Great Britain

[73] Assignee: Quadrant Bioresources Limited, Bedfordshire, England

[21] Appl. No.: 26,695

[22] PCT Filed: Jul. 9, 1986

[86] PCT No.: PCT/GB86/00396

§ 371 Date: May 7, 1987

§ 102(e) Date: May 7, 1987

[87] PCT Pub. No.: WO87/00196

PCT Pub. Date: Jan. 15, 1987

[30] Foreign Application Priority Data

Jul. 9, 1985 [GB] United Kingdom ................ 8517352
May 29, 1986 [GB] United Kingdom ................ 8613066

[51] Int. Cl.$^4$ .............................................. C12N 9/96
[52] U.S. Cl. .................................... 435/188; 424/85.8; 424/88; 435/176; 435/178; 530/350; 530/380; 530/802; 530/830; 536/56; 536/102; 536/112
[58] Field of Search ....................... 435/176, 178, 188; 530/350, 380, 802, 830; 536/56, 102, 112; 424/85, 88

[56] References Cited

U.S. PATENT DOCUMENTS

| | | | |
|---|---|---|---|
| 4,206,200 | 6/1980 | Guthöhrlein et al. | 424/92 |
| 4,457,916 | 7/1984 | Hayashi et al. | 530/351 |
| 4,675,310 | 6/1987 | Chapman et al. | 514/76 |
| 4,762,857 | 8/1988 | Bollin, Jr. et al. | 514/777 |

FOREIGN PATENT DOCUMENTS 0140489 5/1985 European Pat. Off. .
60-149972 8/1985 Japan .

OTHER PUBLICATIONS

Lim et al., "A Study on Environmental Tolerance of Yeast," Misaengmul Hakhoe Chi, 1978, 16(3), 103–10. (CA 92: 126872d).

Loomis et al., "Anhydrobiosis in Nematodes," J. Exp. Zool., 1979, 208(3), 355–60. (CA 91: 87840z).

Primary Examiner—Robert A. Wax
Attorney, Agent, or Firm—Gottlieb, rackman & Reisman

[57] ABSTRACT

Sensitive proteins and other macromolecules, such as enzymes, antibodies, antigens, serum complement, fluorescent proteins, vaccine components, polysaccharides such as agarose etc, can be preserved by drying at ambient temperature and at atmospheric pressure in the presence of trehalose. A porous matrix impregnated with trehalose is provided as a receiver for a blood or other liquid sample to be dried.

12 Claims, 1 Drawing Sheet

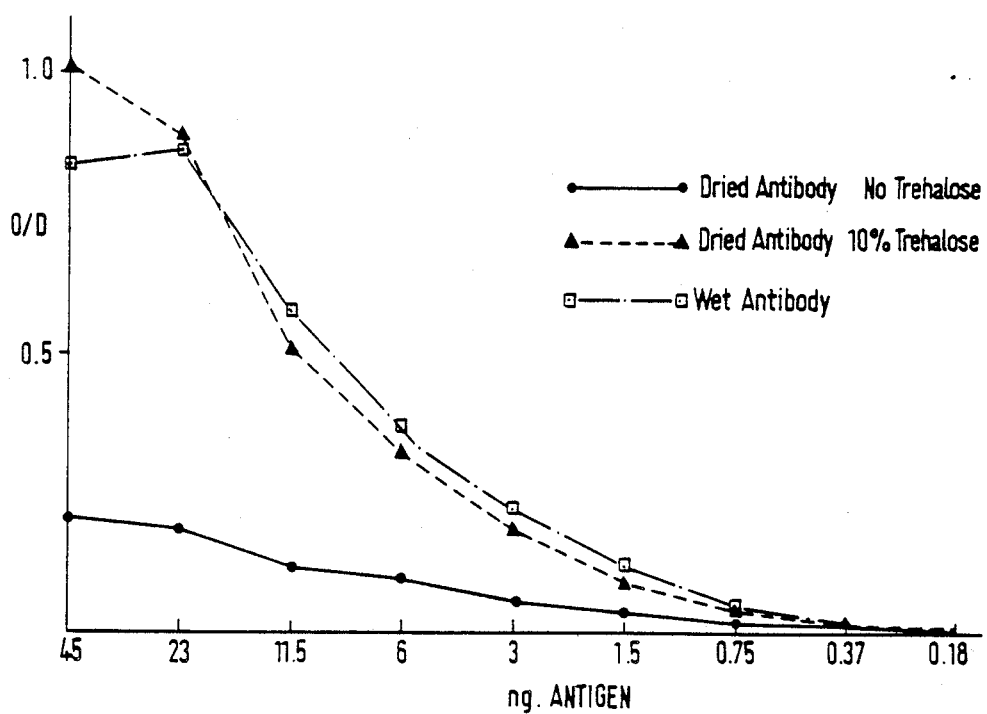

PROTECTION OF PROTEINS AND THE LIKE

This invention relates to the protection of proteins and other macromolecules against denaturing during drying.

Macromolecular compounds, especially proteins and polypeptide-containing compounds, commonly exist in their naturally occurring hydrated state in the form of complex, three-dimentional folded conformations generally known as tertiary structures. Very frequently, the activity of the compound, whether as an enzyme, antibody, antigen, flavourant, fluorescent, gelling agent etc., is critically dependent on the tertiary structure and is severely reduced or even eliminated if the structure is disturbed, even though the chemical empirical formula of the compound may not have changed. This is a very serious problem when the protein etc is required in a dry state, for storage etc.

In order to combat this problem various solutions have been proposed. Enzymes for dry immunoassay kits have been protected in liposomes. Vaccines cannot easily be stored in the freeze-dried state and so have to be stored in bulky ampoules. Fluorescent proteins such as the phycobiliproteins of use in immunoassay techniques lose their ability to fluoresce if dried and so cannot be used in dry kits. Yet a further example is the loss of antigen-binding capacity of monoclonal antibodies bound to a resin substrate and dried.

There is thus an urgent need for a means of protecting such substances from deactivation on drying. We have now found that this object can be achieved by drying the compound in the presence of trehalose.

Trehalose, α-D-glucopyranosyl-α-D-glucopyranoside, is a naturally occurring non-reducing disaccharide which has previously been associated with cell protection. It is known that some organisms, both plant and animal, can resist desiccation to very low levels of body water during drought conditions. These organisms include brine shrimps cysts (Artemia salina), the resurrection plant (Selaginella lepidophylla) and bakers yeast (Saccharomyces cerevisiae). They all share, as a common feature, the presence of large amounts of trehalose in their cells.

A body of work exists on the effects of various carbohydrates including trehalose on the stabilisation of cell membranes during freezing and dehydration. This work shows trehalose to be significantly superior to other carbohydrates in protecting cellular organelles from the deleterious effects of the loss of bound water.

(Crowe, J.H., Crowe L.M. and Mouradian R. (1983) *Cryobiology* 20, 346,356;

Crowe, J.H., Crowe L.M. and Chapman D. (1984) *Archives Biochem. Biophysics* 232, 400–497; and Crowe L.M., Mouradian R, Crowe J.H., Jackson S.A. and Womersley C. (1984). *Biochimia & Biophysica Acta* 769, 141–150.)

While there is no consensus view as to how trehalose exerts it protective effects on cells, one hypothesis is that it substitutes for the bound water on membrane components of the living organism and prevents denaturation due to loss of bound (structural) water. We have now found that the effect is exhibited not only in living cells, but surprisingly also in macromolecules themselves in a purified, isolated state.

EP140489A of Wako Pure Chemical Industries discloses an immunoactive substance (e.g. antibody) on a carrier, e.g. glass beads, stabilized against drying at ambient temperature by immersing in a solution of a sugar, optionally together with a protein such as bovine serum albumin. A considerable number of sugars are mentioned as being of use (ribose, glucose, fructose, mannose, galactose, maltose, lactose, sucrose, oligosaccharides and polysaccharides); preferred are lactose, sucrose or dextrin solutions. There is no mention, however, of trehalose.

Patent Application GB 2009198(A) (Behringwerk AG) discloses the lyophilisation of meningococcal polysaccharide and trehalose; British Patent Application GB 2126588A (Asahi Kasei KKK) discloses the stabilization of tumor necrosis factor (TNF) to lyophilisation and freezing by including either a non-ionic surfactant or trehalose (or another sugar); and Published Japanese Patent Application J 58074696A (Iatron Laboratories) discloses the freeze drying (lyophilisation) of ATP in the presence of trehalose.

It will be noted that these three publications disclose that trehalose will stabilize delicate materials while they are freeze dried. Freeze drying (lyophilisation), as a technique, was devised as being the only way certain sensitive materials can be handled. Ordinary drying at ambient or elevated temperature and at atmospheric or reduced pressure causes irreversible degradation of very many such substances, so much so that it has always gone without saying in the biological field that sensitive proteins etc cannot and must not be dried at ambient temperature. In freeze-drying, the water is removed under high vacuum from the solid material. In this way, the problems of liquid film denaturation of proteins, thermal instability etc are avoided. It has not previously been realised that trehalose can not only provide total protection during drying at ambient temperatures as high as 37° or 40°, but also allow intramolecular electronic processes such as fluorescence and photoconductivity to occur in the dry state.

According to this invention we provide a method of protecting proteins and other macromolecules against denaturation during drying, comprising subjecting an aqueous system containing the protein or the like to drying in the presence of trehalose. The trehalose is conveniently dissolved in the aqueous system and may be present in any effective amount. In general a concentration of from 0.05 to 20% by weight of trehalose is desirable, especially about 0.1 to 10%, e.g. about 2.5% by weight.

The drying process may be achieved by simple air drying of aqueous systems containing the protein and trehalose on a suitable surface, e.g. a glass or plastic plate, or dish, a film of plastic or nitrocellulose or a porous support such as a paper. The drying is preferably at atmospheric pressure.

The presence of the trehalose in the dried product has no effect on the physiochemical or biological properties of the macromolecular substance although there will obviously be rare situations (for example protection of a trehalose-degrading enzyme) where problems will arise. In the case of other enzymes antibodies, antigens and fluorescent markers no problems arise and the compound is as active as if it had been stored in the hydrated state.

Many enzymes are now used in various test procedures, or are themselves tested for in various assays. According to the present invention the enzyme or the substance containing an enzyme can be dried and stored and can be reactivated when required by the addition of water or a buffer solution. For example, peroxidase (e.g.

from horseradish) and alkaline phosphatase (mammalian) can be preserved in this way. The complex "cascade" of enzymes found in serum, which is activated by the antibody-antigen combination in an immune response (P.J. Lachman and M.J. Hobart, "Handbook of Experimental Immunology" ed. D.M.Weir, Blackwell 1978) is notoriously labile. Serum itself contains about 70–75 mg/ml of proteins of which only about 2 mg/ml comprise the complement fraction. Serum containing complement (or a purified complement fraction derived from it) cannot be dried, it has to be stored under very low temperature conditions ($-70°$ to $196°$ C.). It can be lyophylised, but even this technique destroys some of the activity. Thus, for example, lyophylised complement cannot be used in lymphocyte cytotoxicity assays. Most surprisingly, we find that complement activity can be completely preserved according to the present invention by drying in air at room temperature. The dried material can be stored at, say $37°$ C. for weeks and can be reconstituted with its activity retained.

We find that the amount of trehalose required to be present in the serum sample is generally proportional to the content of protein. For example a 50% by weight serum dilution in water requires at least 0.22M trehalose (i.e. about 75g/l) while a 25% dilution requires at least 0.15M trehalose (i.e. about 51g/l) for complement protection. Other serum components e.g. serum antibodies need rather less. In general, therefore, a weight ratio of trehalose to protein (or other macromolecule) of at least 1.4:1, preferably at least 2:1 and most preferably at least 3:1 is suitable, e.g. up to 10:1.

The preservation of serum and serum complement, antibodies and antigens, means that according to the present invention it is also possible to preserve many types of vaccine by drying in the presence of trehalose. Antisera are used to treat various toxic conditions and immunising vaccines containing killed microorganisms are widely used. Both types of vaccine require storage under cool, hydrated conditions, or under deep freeze conditions. Dried vaccines are now possible by the technique of this invention.

Another problem of storage and preservation occurs in the field of agarose gels. For many biochemical techniques agarose gels are used as substrate, e.g. electrophoresis, Ouchterlony diffusion, immunoelectrophoresis etc. Gels of 1–3% are widely used as separation media in these techniques. At the present time they have to be made fresh in the laboratory for each experiment by heating solid agarose in buffer until it dissolves, then pouring the molten agarose into a former and cooling to gel the agarose. Pre-formed gels can only be stored for relatively brief periods in humidified containers. If allowed to dry, the gels undergo irreversible collapse of gel structure and cannot be reconstituted by simple rehydration in water or buffer.

According to the present invention 2 and 3% agarose gels containing 2–20% trehalose can be dried and subsequently rehydrated. We have compared their rehydration characteristics with gels dried without trehalose we have found that the dried gels can be completely rehydrated to give gels of the original depth and water content. This means that dried agarose gel plates can be kept indefinitely without the need for special containers and can simply be rehydrated when required for use.

According to the invention it is also possible to preserve by drying at ambient temperatures fixed whole red blood cells and especially fixed whole red blood cells to which are attached labile molecules such as antibodies, and antigens, e.g. for use in the extremely sensitive form of immunoassay known as the haemagglutination assay. In this, either antigen or antibody is coupled chemically to the surface membrane or erythrocytes and the appropriate ligand can be detected by its ability to cause the red cells to clump together into a visible aggregation pattern. Where antigen is coupled to the red cell, the potency of an antibody can be assessed by titrating the antibody out in dilution steps and observing the point at which it no longer causes agglutination/aggregation of the red blood cells. Where antibody is coupled to the red cell, the precise amount of antigen in an unknown solution e.g. blood can be estimated by detecting the titration end point as above. For this to work, the antigen must carry more than one antigen site per molecule capable of being "seen" by the antibody on the red cells.

This assay requires a lot of preparation. The red cells are usually used fresh and need to be washed, chemically coupled with either antigen or antibody and then added to the titrated dilution of ligand.

We have found that we can couple antigens and antibodies to red cells which are fixed with a histological fixative such as glutaraldehyde and then dry the coupled red cells in the presence of trehalose. Upon rehydration the coupled, fixed red cells can be resuspended to form a perfect single cell suspension which then behaves as a fresh red cell suspension does in haemagglutination assays. In this use the trehalose serves two functions:

1. It completely preserves the function of the antibody or antigen coupled to the fixed red cell membrane.

2. It completely preserves the fixed red cells themselves so that they completely resuspend in buffer to give a single cell suspension. When fixed red cells are dried in the absence of trehalose they undergo irreversible spontaneous agglutination and cannot be used.

Thus an instant haemagglutination assay kit can be constructed in the dry state which works in an entirely conventional way when the antigen or antibody which is to be measured is simply added to the dried red cells in buffer.

R Phycoerythrin is a phycobiliprotein which can be easily purified from the marine rhodophyte, Rhodymenia. It is brilliantly fluorescent in the red-orange with an emission maximum of 575 nm. Its bright fluorescence and high quantum yield are dependent upon the spatial distribution and configuration of the phycourobilin and phycoerythrobilin chromophores in the molecule. This fluorescent protein of choice for many fluorescent assays because it is 20 times brighter than fluorescein on a molar basis and can easily be coupled to probes such as antibody or Avidin/Streptavidin for use in fluorescent antibody or DNA/RNA hybridisation assays.

A serious drawback to the use of this reagent is its susceptibility to fluorescence fading in aqueous solution. This gives the fluorescence a very short half life. It is thought to be due to damage to the phycoerythrin molecule due to the creation of free radicals in the aqueous solvent when illuminated with the exciting wavelength for fluorescence. Drying the molecule prevents creation of free radicals and therefore the fading but destroys more than 90% of the fluorescence because the three dimensional structure of this large protein (240 Kd), upon which its fluorescent properties depend, collapses when dried.

We have found that this molecule can be dried completely in the presence of trehalose without loss of its fluorescent properties. This means that this protein can now be used in assays which require prolonged or repeated exposure to high intensities of exciting light without fading and with complete retention of its intense fluorescence. Fading can be reestablished by washing away the trehalose and irradiating the molecule in an aqueous solvent.

A major requirement for the preservation of protein structure and function is in blood samples taken for clinical measurement of levels of antibodies, antigens and enzymes. At present these samples are usually stored for short periods of 4° or for prolonged periods at −20° or lower in deep freeze. They cannot be dried.

An attractive alternative would be to store serum or blood samples in the dry form where the structure and function of the blood components were protected by drying in the presence of trehalose. A simple and elegant method of achieving this is to use, as the sample storage medium, a porous matrix previously impregnated with trehalose, on to which the blood or serum sample is applied and which is allowed to dry again. The drying can be effected at any convenient ambient temperature, e.g. those encountered in tropical areas. The content of the trehalose in the matrix is conveniently from 5 to 25% by weight of dry matrix, e.g. 7.5 to 20%. The matrix may comprise any suitable inert material, e.g. cellulose or glass-based papers, porous plastic films, fabrics etc. For ease of use, cellulose filter papers are preferred. For ease of retrieval of the absorbed protein, the matrix is conveniently a thin sheet or web.

While we do not wish to be bound by theory, it seems likely that the unique properties of trehalose in preserving the structure and function of proteins and other macromolecules in the dry state is due to hydrogen bonding of trehalose molecules via their hydroxyl groups, to appropriate groups on the macromolecule. In this way trehalose takes the place of structural (bound) water molecules so that there is no collapse of macromolecular structure upon drying. The trehalose acts as a dry scaffold maintaining the structural integrity of the macromolecule.

Many macromolecular functions require mobility of the macromolecule e.g. antibodies have to physically move into close proximity to their antigen in order for binding to occur through electrostatic and hydrophobic interactions. The same is true of enzymes binding their substrates. Minor molecular motion is also required for other macromolecular functions. Thus haemoglobin undergoes rotation and movement of certain amino acids during the reversible binding of oxygen and carbon dioxide. None of this molecular mobility is observed in the dry state. Thus we have dried haemoglobin in the oxy and carboxy forms, and these molecules retain their spectral properties when dried in the presence of trehalose.

Exposure of carboxy haemoglobin, dried in trehalose, to 100% oxygen does not result in conversion to the oxy form whereas this occurs within a few minutes in aqueous solution. In contrast, the fluorescence of R-phycoerythrin involves "movement" only on the sub atomic level. Absorption of light energy at low wavelengths e.g. (488 nm) causes electrons in the chromophores to shift to higher energy orbits. Fluorescence at longer wavelengths is due to the emission of photons when these electrons jump back to lower energy orbits. The preservation of the fluorescence of R-phycoerythrin in the dried state by trehalose thus indicates that electronic properties of macromolecules can be completely preserved by this technique. This method is therefore of great interest in the application of biological (and synthetic) macromolecules in new electronic applications. Examples include proton and electron pumping (such as is mediated, on exposure to light, by bacteriorhodopsin and rhodopsin). The ability to dry proteins and other macromolecules and preserve their three dimensional shape and functions offers the possibility of molecular electronics including direct conversion of solar energy into hydrogen or electric current using biological molecules which have an inherently high efficiency and the construction of sensors and electronic circuits (including computers) on the molecular size scale.

The following Examples illustrate the invention further.

EXAMPLE 1

The phycobiliprotein R-phycoerythrin was purified from a marine Rhodophyte. This brilliantly fluorescent red protein was blotted onto nitrocellulose membrane or glass fibre filter paper in phosphate buffer with and without 10% w/v added trehalose and dried at room temperature. In the absence of trehalose the red protein turned purple and lost its ability to fluoresce orange/red when illuminated with blue light. In the presence of 10% trehalose the protein retained its colour, and fluoresced just as brightly as the protein in solution, even though it was completely dry.

We have also completely preserved the fluorescence of phycoerythrin coupled to antibodies which have bound to the surface of lymphocytes, by drying them in the presence of trehalose.

EXAMPLE 2

We have also studied the ability of trehalose to preserve the antigen-binding capacity of antibodies when dried. This can best be illustrated by its application to a very sensitive two site Enzyme Linked Immunoassay (ELISA) for Class I transplantation antigens.

In this assay a monoclonal antibody YR5/310 was bound to polystyrene surfaces in a 96 well microtitre plate (Nuc Immunoplate) by overnight incubation. We then dried 24 wells of the plate in the absence of trehalose, dried 24 wells in the presence of 10% added trehalose and left 48 wells wet in phosphate buffer. The drying was at 37° overnight.

We then added serum containing the relevant class I molecules and incubated at room temperature for 5 hr. The plates were washed and then a second antibody, YR5/12, labelled with biotin was added for 1 hr. The plates were washed again and incubated with the substrate 3,3',5,5'-tetramethyl benzidine for 20 min. The reaction product was then measured in an automatic ELISA plate reader. The results (FIG. 1) show that drying the bound antibody in the absence of trehalose causes a loss of >90% of the binding activity while drying in the presence of added trehalose preserves the antibody activity completely so that it gives ELISA results comparable to those given by non dried antibodies.

EXAMPLE 3

Dry plate blood typing assay

A four well tissue culture dish (Nunclon 3/132 multidish 3,Nunc Denmark) is used. Other cheaper alternatives could be used, e.g. "blister packs" made from thin PVS sheet. Also Standard microtitre plates of 94, 48 or 24 wells could also be used.

Manufacture

Three wells contain antibody and one (well 4) contains only 50μl of monoclonal mouse IgM antibody to the A blood group substance (64 i.u. per ml—from the Blood Group Reference Laboratory, Radcliffe Infirmary, Oxford.)

Well 2 contains 50μl of monoclonal mouse IgM antibody to the B blood group substance (64 i.u. per ml—same source as above).

Well 3 contains 50μl of monoclonal human IgM antibody to the Rh D antigen (1 mg per ml, produced in our laboratory).

All wells also contain 50μl of 0.1% to 10% w/v trehalose solution in distilled water plus 5 units of heparin and 0.01% sodium azide. The plates are dried overnight at 37° C. in a warm room. They can then be stored at room temperature indefinitely.

Use

Add 2 drops (approx 100μl) of water (distilled or tap water) to each well and spread by rocking plate for 2-5 sec. Add 1 drop of whole blood and rock gently to mix blood and well contents. Rock gently every few seconds for 5 min.

Results

Blood containing red cells which are positive for the A, B or Rh antigen will give a clear, coarse macroscopic agglutination pattern within 30 secs in the appropriate well(s). O, Rh-ve blood gives to agglutination in any well.

Advantages

1. The plates are indefinitely stable at room temperature. They have been stored at 37° for 2 months without loss of activity.
2. The test is very convenient and fast. No equipment is required. Whole blood is used. The erythrocytes do not need to be separated or washed. A finger prick will give enough blood for ABO and Rh testing.
3. Trehalose preserves 100% of the antibody activity. A test of five sugars all used at 5% final concentration in a titrated haemagglutination assay gave the following results.

|  | % activity retained in HA titre |
|---|---|
| Wet antibody (a human IgM anti-D) | 100 |
| Dried Ab + no additive | 3.7 |
| Dried Ab + trehalose | 100 |
| Dried Ab + maltose | 11.1 |
| Dried Ab + sucrose | 11.1 |
| Dried Ab + raffinose | 3.7 |
| Dried Ab + glucose | 1.2 |

An additional titration was done to establish whether there is an optimum concentration of trehalose for preservation. The antibodies tested were mouse monoclonal IgM anti A antibody, a mouse monoclonal IgM anti B antibody and a human monoclonal IgM anti Rh antibody used above. They were diluted to an appropriate starting concentration as follows: mouse anti A 1:10, mouse anti B 1:10, human anti Rh (to a final concentration of 20μg/ml). These were titrated 1:3 across a 96 well microtitre plate in Dulbecco's phosphate buffered saline (PBS) in a final volume of 50μl. To each horizontal 8 well row was added 50μl of trehalose at concentrations ranging from 10% w/v to 0.1% w/v. The wells were then dried at 37° overnight. Next day the wells were rehydrated with 100μl distilled water containing buffer sufficient to restore isotonicity. Then 50μl aliquots were transferred to a v-bottom microtitre plate and 25μl of 1% washed human red cells carrying the appropriate blood group antigens added and mixed. Haemagglutination titres were read after 2-3 hours at room temperature. The results showed that with the human antibody maximum preservation of activity was 100% and occurred at 2.5% final concentration of trehalose at the drying stage. There was a slight decrease in titre at 5% final trehalose concentration. With the anti A antibody any trehalose concentration above 1% preserved maximal activity and with the anti B antibody any concentration above 0.5% preserved maximum activity.

Note

Many other antibodies, both monoclonal and serum antibodies of the IgM or IgG class have been preserved in this way with trehalose. Preservation of activity is always 100% or close to it. The antibody can be either bound to the plastic surface of the well of the titre plate by hydrophobic and charge interaction or can be bound to nitrocellulose or nylon membrane by similar forces or can be free in solution. In all cases the activity is preserved. Where the antibody is free in solution its function is fully retained i.e. agglutinating anti blood group substance antibodies cause vigorous agglutination of the red cells are drying, showing that they retain their capacity for multivalent binding and rehydrating in solution.

EXAMPLE 4

Protection of the antibody activity in whole serum by drying in the presence of trehalose A sheep antiserum to rat IgG immunoglobulin (K237) was titrated in a 96 well flat bottom microtitre plate as 1:3 steps (25μl serum in 50μl PBS). 50μl of 5% w/v trehalose in D.W was then added and the plate dried at 37° in a warm room for 48 hr.

The wells were reconstituted with 100μl distilled water. 50μl of the contents of each well were transferred to v bottom microtitre plates, DA rate erythrocytes were washed ×3 in saline and sensitized by incubation for 2 hr at RT with tissue culture supernatant of the monoclonal antibody R3/13 HLK which is specific for the $A^a$ class 1 transplantation antigen on DA erythrocytes. The red cells were then washed x3 in saline and resuspended at 1% v/v in PBS +1% BSA. The sensitized rat erythrocytes were added. At the same time fresh K237 serum was titrated as above as a positive non-dried control.

The capacity for the dried and fresh serum to cause indirect agglutination of the red cells sensitized by the rat antibody R3/13 was then read.

| | | Results | |
|---|---|---|---|
| Row | Treatment | Titre (cups) | Titre (dilution) |
| A | Dried + Trehalose | 7 | 1:8,748 |
| B | Dried + Trehalose | 7 | " |
| C | Dried + Trehalose | 7 | " |
| D | Dried + Trehalose | 7 | " |
| E | Fresh titration | 7 | " |

-continued

| Row | Treatment | Results Titre (cups) | Titre (dilution) |
|---|---|---|---|
| F | Fresh titration | 7 | " |
| G | Fresh titration | 7 | " |
| H | Fresh titration | 7 | " |
| A | Dried (no Trehalose) | 2 | 1:36 |
| B | Dried (no Trehalose) | 1 | 1:12 |
| C | Dried (no Trehalose) | 1 | 1:12 |
| D | Dried (no Trehalose) | 2 | 1:36 |

Conclusions

Trehalose preserves 100% of the antibody activity of the whole serum. Drying in the absence of trehalose destroys >99% of the activity.

EXAMPLE 5

A number of different matrices were examined for use as a trehalose support. They include pure cellulose paper (Whatman No. 1 filter paper), glass fibre paper (What man GF/A and GF/C papers), polyurethane sponge foam and porous polyethylene sheet. These matrices were soaked in trehalose dissolved in distilled water at various concentrations from 10% down to 1% and dried at 37°. It was found that the content of trehalose in the dried paper was about twice that in the solution. Thus a 10% solution gave dry paper containing 20% by weight of trehalose and a 5% solution gave paper containing 10% by weight of trehalose. Various sera were applied to the paper and dried at 37°. After various periods of storage at 37+, samples were eluted with distilled water or normal saline; usually used in a volume 2-4 times that of the original serum sample so that their potency could be directly compared with fresh non-dried samples of the same sera.

K237, a sheep antiserum against rat IgG, was dried on to 10% trehalose-impregnated cellulose paper, glass fibre paper and porous polyethylene sheet and stored for 7 days at 37° C.

The paper or sheet was eluted with 4 volumes of normal saline and titrated in an indirect haemagllutination assay for its ability to agglutinate DA strain rat erythrocytes coated with a monoclonal antibody (JN2/85) against the class 1 antigens expressed on the erythrocyte membranes. The results show that 100% of the activity was preserved on cellulose paper and on porous polyethylene sheet, and 50% on glass fibre paper.

| Paper | Titre |
|---|---|
| Schleicher & Schull GB003 | 1:640 |
| Schleicher & Schull GB002SB | 1:640 |
| Whatman GF/C (Glass fibre) | 1:1280 |
| Whatman No.1 (Cellulose) | 1:2560 |
| Porous Polyethylene Sheet | 1:2560 |
| (non-dried antiserum | 1:2560) |

The same antiserum was then tested by drying on the Whatman No. 1 cellulose paper in the presence of various sugars and in the absence of sugar.

| Sugar | Titre |
|---|---|
| Sucrose | 1:640 |
| Raffinose | 1:640 |
| Trehalose | 1:1280 |
| Nil | 1:640 |
| Wet antiserum | 1:1280 |

Note that a drop in titre from 1:1280 to 1:640 means at least 50% of antibody activity is lost. No significant difference exists between the sucrose and raffinose papers and the untreated paper.

EXAMPLE 6

Drying phycoerythrin on paper or membranes

R-phycoerythrin at 5 mg/ml was dried at 37° on glass fibre filter paper (Whatman GF/C), cellulose filter paper (Whatman No. 1) or on nitrocellulose membrane (Schleicher & Schull 0.45μ pore size) in the presence of 5% trehalose in solution and in its absence. In the absence of trehalose the spots of dried R-phycoerythrin changed colour to a purplish red and lost >90% of their fluorescence intensity. In the presence of added trehalose they retained both colour and fluorescence. The trehalose-containing samples were stored in the dark for 10 months without loss of fluorescence.

EXAMPLE 7

Use of membrane-dried phycoerythrin in a novel assay for probing DNA on nitrocellulose membranes.

Because fluorescence of phycoerythrin can be excited in the dry state on membranes without fading, a very strong integral fluorescent signal can be recorded on photographic emulsion from this molecule.

As an example of the sensitivity of this method, 10 fold serial dilutions of DNA from 100 picogram to 0.1 pg were dried onto nitrocellulose membranes using a slot-blot apparatus. This DNA had been labelled with biotin using photobiotin. These membranes were probed with streptavidin covalently coupled to R-phycoerythrin (QB-AR 4 Serotec Ltd.) by incubation for 1 hr at room temperature in a 1 mg/ml solution followed by extensive washing overnight in 300 ml of blocking buffer (1% BSA in PBS). The membranes were then washed in a solution of 10% trehalose in distilled water and dried at room temperature. The membranes were then photographed using a 1 hr exposure in a modified Polaroid VDU camera while illuminated with intense blue light from a xenon light source passed through 490 nm interference filters (Ealing Beck). The camera lens was covered with a long pass interference filter with a 560 nm cutoff so that only the orange-red fluorescence was recorded. The blots of labelled DNA was readily detected with a sensitivity of >10 pg DNA and negligible background. The same dried membrane of nitrocellulose was photographed with this system more than 20 times over a three day period without significant fading of the fluorescence signal. In contrast, when illuminated wet and in the absence of trehalose, the fluorescence signal fades within about 30 seconds. Drying in the absence of trehalose leads to loss of the fluorescent signal.

EXAMPLE 8

Fluorescence microscopy of rat lymphocytes

Fluorescence microscopy using R-phycoerythrin as the fluorochrome was previously very inefficient because of fluorescence fading in aqueous mountants. This can be prevented by drying of the preparation and mounting in a non-polar mountant such as Gurr's Fluoromount, but drying destroys more than 90% of the fluorescence of R-phycoerythrin. This is prevented by drying in the presence of trehalose in the final buffer. This preserves virtually all of the fluorescence intensity of the labelled cells or tissues which can be mounted in an organic non-aqueous mountant and repeatedly examined for prolonged periods without loss of fluorescent signal.

The anti CD4 monoclonal antibody W3/25 was coupled with biotin-linker-arm N-hydroxysuccinimide ester and used in saturating doses to label the T helper subset of rat lymphocytes. These labelled cells were then detected with a second stage staining using a streptavidin-R-phycoerythrin conjugate. After a final wash the cells were divided into four aliquots and one was examined in the FACS to illustrate correct labelling with these reagents. Two other aliquots were spun down and resuspended in serum which either contained 10% added trehalose or did not. Smears were made and dried and then mounted in Fluoromount. The fourth aliquot was mounted wet in PBS. All three preparations were examined in a Zeiss photomicroscope II with Ploem optics.

The wet amount showed about 75% brilliantly fluorescent cells which faded rapidly so that within about 20–30 secs only the brightest cells could be barely discerned. The dried mount which did not contain trehalose showed only very weakly fluorescent cells which could barely be seen above the background.

The preparation dried with added trehalose showed 75% brilliantly fluorescent cells which did not fade. This preparation was repeatedly examined over several weeks and showed no detectable fading of the labelled cells.

Thus trehalose preserves completely several widely divergent and very labile properties of protein molecules even when they are completely dried. These properties (fluorescence and antigen binding) depend completely on the preservation of an intact tertiary structure of the molecules.

This phenomenon means that the functions and structures of proteins can now be completely preserved in the dry state. Thus proteins of scientific or medical interest can be preserved without the requirements of freezing or freeze-drying. Kits for immuno- assays can be prepared and stored dry without the need for sealing or liposome-formation to prevent water loss. Proteins and other molecules with novel and unusual properties such as chemiluminescence, conduction of electric currents and even possibly complex properties such as nitrogen fixation or photosynthesis may be preserved in the dry state.

EXAMPLE 9

Preservation of enzyme activity

The mammalian enzyme alkaline phosphate from calf intestine was serially diluted in phosphate buffered saline (PBS) and added to the wells of a NUNC Immunoplate. After overnight incubation to bind the enzyme to the plastic surface, the wells were washed, shaken free of liquid, and dried at 37° in the presence or absence of 5% trehalose in distilled water. The plates were then incubated at room temperature for 4 weeks. At the end of this time the wells were rehydrated with distilled water and substrate added. A positive control consisted of fresh dilutions of the enzyme. The activity of one enzyme was measured by the standard test of reducing p-nitrophenylphosphate and monitoring the optical density at 405 nm.

Full retention of activity was obtained when the enzyme was dried with trehalose, compared with over 90% loss of activity when it was dried in the absence of trehalose. Identical results were obtained with horseradish peroxidase when used in identical experiments.

EXAMPLE 10

Preservation of Serum Complement

Guinea pig serum was prepared fresh and frozen in aliquots at −196° until use. As target cells, washed sheep erythrocytes (SRBC) which had been stored in Alsever's solution for up to 2 weeks were incubated with the bovine monoclonal anti-Forrsman antibody 94A1-AZA for 1 hr at 4° and then washed in complement fixation diluent (CFD).

Freshly thawed guinea pig serum was diluted in CFD where required in flat bottom microtitre plate (NUNC, Denmark) and trehalose added at various concentrations. The plates were dried under a stream of dry air at room temperature overnight.

For the CH50 assay (P.J. Lachmann and M.J. Hobart in "Handbook of Experimental Immunology" ed. D.M. Weir, Blackwell 1978), dried or fresh complement was titrated out in a U bottom microtitre plate and sensitised SRBC added to a final concentration of 2%. The plates were then incubated at 37° for 1 hr and centrifuged. The endpoint was measured as the cup in which 50% of the erythrocytes remained as a button.

Results

The protective effect of trehalose depended upon the molar ratio of sugar to protein. Thus 100% of complement activity was preserved in 50% normal serum by trehalose at 0.22M and above, in 25% serum this required 0.15M and above. High concentrations of trehalose (up to 0.5M) were not inhibitory at any concentration of serum.

Drying of neat serum in the absence of trehalose caused a loss of 75% of the complement activity. Drying of 25% serum in the absence of trehalose caused a loss of 93% of complement activity. Those loses were completely prevented by trehalose, the activity of dried and reconstituted complement being exactly equivalent to fresh complement.

EXAMPLE 11

Agarose gels

We have dried 2 and 3% agarose gels containing 2-20% trehalose and compared their rehydration characteristics with gels dried without trehalose. The extent of rehydration was measured by weighing the gels to establish the amount of water regained. Their suitability as separation media was established by preparing Ouchterlony double diffusion assays and immunoelectrophoresis in the rehydrated, trehalose-preserved, dried gels.

The results (Table) show 100% water regain by 2% and 3% gels dried from 5% or 10% trehalose. These gels are identical in appearance with freshly poured and solidified gels.

Both Ouchterlony diffusion and immunoelectrophoresis can be performed in such gels with results which are identical to assays performed in fresh gels. By varying the buffer in which the gels are reconstituted, the same gel, dried from agarose/trehalose in distilled water, can be used for a variety of purposes. Thus Ouchterlony buffer makes the gel suitable for this assay wile electrophoresis buffer enables electrophoresis or immunoelectrophoresis to be performed.

TABLE

| % Trehalose | | Fresh Gel | Dry Film | Rehydrated Gel | Recovery % |
|---|---|---|---|---|---|
| 2% Agarose | 5 | 1.721 | 0.170 | 1.733 | 100 |
| 10 | | 2.390 | 0.345 | 2.371 | 99 |
| 0 | | 2.08 | 0.067 | 0.727 | 35 |
| 3% Agarose | 5 | 2.126 | 0.220 | 2.170 | 102 |
| 10 | | 2.280 | 0.343 | 2.352 | 103 |
| 0 | | 1.984 | 0.079 | 0.717 | 36 |

This technique means that agarose gels can be prepared in advance, dried and stored at room temperature indefinitely and can be reconstituted within 1 hr by soaking in buffer and used immediately.

I claim:

1. A method of protecting proteins or other biological macromolecules against denaturation during drying, comprising subjecting an aqueous system containing the protein or other biological macromolecule to drying at a temperature above freezing in the presence of trehalose in an amount between about 0.05 and 20 weight percent based on the total weight of said aqueous system.

2. A method according to claim 1, in which the ratio of trehalose to protein or other biological macromolecule is at least 1.4:1 by weight.

3. A method according to claim 1, in which the protein or other biological macromolecule forms part of a substance selected from the group including an enzyme serum, serum complement, an antibody, an antigen, a fluorescent protein, a vaccine component and a polysaccharide.

4. A method according to claim 1, in which the system is dried at ambient temperature or above and at atmospheric pressure.

5. A product dried at a temperature above freezing containing trehalose and a protein or other biological macromolecule in a weight ratio of at least 1.4:1 respectively.

6. A dried product according to claim 5 containing an enzyme, serum complement, an antibody or antigen, a fluorescent protein, a vaccine component or a polysaccharide.

7. A plate having adhered thereto one or more antibodies dried at a temperature above freezing in the presence of trehalose in an amount at least about 1.4 times greater by weight than the amount of said one or more antibodies.

8. The method of claim 1, wherein the presence of trehalose is impregnated into a porous matrix.

9. The method of claim 8, wherein said porous matrix contains 5–25% by weight trehalose based on the total weight of said porous matrix.

10. The method of claim 8, wherein the porous matrix comprises a cellulose or glass-based paper, a porous plastic film, or a fabric.

11. A method for protecting a protein or other biological macromolecule against denaturation during drying comprising subjecting an aqueous system containing said protein or other biological macromolecule to drying at a temperature above freezing in the presence of trehalose in an amount of at least about 1.4 time greater by weight than the amount of said protein or other biological macromolecule.

12. A method for protecting a protein or other biological macromolecule against denaturation during drying comprising subjecting an aqueous system containing said protein or other biological macromolecule to drying at a temperature above freezing in the presence of trehalose in an amount of at least about 0.05 weight percent based on the total weight of said aqueous system.

* * * * *